(12) United States Patent
Clark et al.

(10) Patent No.: US 7,906,662 B2
(45) Date of Patent: Mar. 15, 2011

(54) PROCESS FOR THE PREPARATION OF CYCLOPROPYL CARBOXYLIC ACID ESTERS AND DERIVATIVES

(75) Inventors: Adrian Clark, Södertälje (SE); Elfyn Jones, Södertälje (SE); Ulf Larsson, Södertälje (SE); Anna Minidis, Södertälje (SE)

(73) Assignee: Astrazeneca AB, Sodertalje (SE)

( * ) Notice: Subject to any disclaimer, the term of this patent is extended or adjusted under 35 U.S.C. 154(b) by 1092 days.

(21) Appl. No.: 11/487,457

(22) Filed: Jul. 17, 2006

(65) Prior Publication Data

US 2006/0258879 A1 Nov. 16, 2006

Related U.S. Application Data

(63) Continuation of application No. 10/275,547, filed on Nov. 7, 2002, now Pat. No. 7,122,695.

(51) Int. Cl.
C07C 65/17 (2006.01)
C07C 247/22 (2006.01)
(52) U.S. Cl. .......................................... 552/6; 562/470
(58) Field of Classification Search .................. 562/470; 552/6; 564/307
See application file for complete search history.

(56) References Cited

U.S. PATENT DOCUMENTS

| 4,767,777 A | 8/1988 | Bass et al. |
| 5,286,736 A | 2/1994 | Soyka et al. |
| 5,929,291 A | 7/1999 | Bajgrowicz et al. |

FOREIGN PATENT DOCUMENTS

| GB | 873 018 A | 7/1961 |
| WO | WO 98/57640 A1 | 12/1998 |
| WO | 9905143 A1 | 2/1999 |
| WO | WO 99/05143 A1 | 2/1999 |

OTHER PUBLICATIONS

Evans, D.A., et al; "A Convergent Total Synthesis of (+−)-Colchicine and (+−) Desacetamidoisocolchicine"; J. Am. Chem. Soc.; vol. 103, No. 19, pp. 5813-5821 (1981); XP002476378.
Orr, F.G., "Inhibition o furidine Phosphorylase: Synthesis and Structure-Activity Relationships of Aryl-Substituted 5-Benzyluracils and 1-[(2-Hydroxyethoxy)methyl]-5-benzyluracils"; et al; J. Med. Chem., vol. 38, No. 19; pp. 3850-3856 (1995) XP002476381.
Journal of the American chemicals society, vol. 87, 1965, E.J. Vorey et al, "Dimethyloxosulfonium Methylide ((CH3)2S0CH2) and Dimethylsulfonium Methlide ((CH3)2S0CH2). Formation and Application to Organic Synthesis" p. 1353-p. 1364.
Advancedd Organic Chemistry, Fourth Edition, Jerry Mark, Reactions, Mechanisms, and structure, John Wiley & Sons, New York, 1992, pp. 872, 741 pp. 428-429, pp. 1091-1095.
Organic Chemisty, Fifth Edition, T.W. Graham Solomons, John Wiley & Sons, Inc., New York, 1992, pp. 781-782, p. 775, pp. 846-848; pp. 830-832; pp. 834-835.
STN International, File CAPLUS, CAPLUS accession No. 1998:429075, Document No. 129:135904 Diaz-Requejo et al: "BpCu-Catalyzed Cyclopropanation of Olefins: A simple System That operates under andHeterogeneous Conditions (BP = Dihydridobis (pyraxoly)borate)"; Organometallics (1998), 17(14), 3051-3057, RN 91393-54-3.
STN International, File CAPLUS, CAPLUS accession No. 1998:250346, Document No. 128:321223,Galardon, Erwan et al: "Asymmetric Cyclopropanation of a alkenes and diazocarbonyl insertion into S-H bonds catalyzed by a chiral porphyrin Ru(II) complex"; Tetrahedron Lett. (1998), 39(16), 2333-2334, Rn 207279-36-5.
STN International, File CAPLUS, CAPLUS accession No. 1995:927375, Document No. 124:116326, Demonceau, A. et al: "Cyclopropanation catalyzed by RuC13 (PPh3) and OsC12(PPh3)3"; Tetrahedron Lett. (1995), 36(46), 8419-22, RN 4103-56-4, 4103-57-5.
STN International, File CAPLUS, CAPLUS accession No. 1995:597880, Document No. 123:169063, Demonceau, A. et al: "Cyclopropanation of activated olefins catalyzed by Ru-phosphine complexes"; Tetrahedron Lett. (1995), 36(20), 3519-22, RN 4103-56-4, 4103-57-5.
STN International, File CAPLUS, CAPLUS accession No. 1998:200362, Document No. 128:270257, Kusuyama, Yoshiaki: "Solvolysis of 1-(trans-2-(m-or p-substituted phenyl) cyclopropyl)-1-methyl-ethyl p-nitrobensoates"; Bull. Chem Soc. Jpn. (1998), 71(3), 685-691, RN 4103-57-5, 205674-79-9.
Chemical Abstracts, vol. 59 (1962), (Columbus, Ohio, USA), Kaiser, Carl et al, "2-Substituted cyclopropylamines. I. Derivatives and analogs of 2-phenylcyclopropylamine", The Abstract No. 504f, Med Pharm. Chem. 1962, 5, 1243-1265, RN 91329-59-8, 91393-53-2, 92576-45-9.
STN International, File CAPLUS, CAPLUS accession No. 2000:6701, Document No. 132:122310, Wu, Xin-Yan et al: "Asymmetric synthesis of 5-hydroxtryptamine recepter agonist (1R,2S)-(−)-2-(2-hydroxyphenyl)-N, N-dipropyl-cyclopropamine"; & Gaodeng Xuexiao Huaxue Xuebao (1999), 20(12), 1982-1896, RN256431-75-1, 256431-73-9.
Chemical Abstract, vol. 57 (1962), (Columbus, Ohio, USA), Richard Fuchs et al, "Transmision of electronic effects by the cyclopropane ring.Ionization constants of m- and p-substituted.bet.-phenylpropionic, cis-and trans-2-phenylcyclopropanecarboxylic acids in 50% ethanol", The Abstract No. 3347I, J. Org. Chem. 1962, 27 733-736, RN 91329-60-1.
STN International, File CAPLUS, CAPLUS accession No. 1996:148289, Document No. 124:250558, Vallgaarda, Jerk et al: "trans-2-Aryl-N,N-dipropyl-cyclopropylamines: Synthesi and Interaction with 5-HT 1A Receptors"; & J. Med Chem. (1996), 39(7), 1485-93, RN175168-73-7.
Roberts et al, Basic Principles of Organic Chemistry, W.A. Benjamin, Inc., pp. 530-531 and 562 (1965).
Kaiser et al, J. Organic. Chem., vol. 30, p. 3972-3975 (1965).
Corey et al, JACS, 87:6, pp. 1353-1364 (1965).

(Continued)

Primary Examiner — Bernard Dentz
(74) Attorney, Agent, or Firm — Nixon & Vanderhye

(57) ABSTRACT

The compounds trans-(1R,2R)-2-(3,4-difluorophenyl)cyclopropanecarbonyl azide and trans-(1R,2S)-2-(3,4-difluorophenyl)cyclopropanaminium (2R)-2-hydroxy-2-phenylethanoate.

1 Claim, No Drawings

OTHER PUBLICATIONS

The Merck Index, Merck & Co., p. ONR-60 (1976).

Spence, E.L., et al; "*Cis-Trans* Isomerization of a Cyclopropyl Radical Trap Catalyzed by Extradiol Catechol Dioxygenases: Evidence for a Semiquinone Intermediate"; *J. Am. Chem. Soc.;* vol. 118, No. 35, pp. 8336-8343 (1996); XP002476377.

Corey, E.J., et al; "Dimethyloxosulfonium Methylide (($CH_3)_2$soch$_2$) and Dimethylsulfonium Methylide (($CH_3)_2SCH_2$). Formation and Application to Organic Synthesis"; *Journal of the American Chemical Society,* vol. 87, pp. 1353-1364 (1965); XP000916647.

March, J.; "Advanced Organic Chemistry"; New York, John Wiley & Sons, US; pp. 738-741, 428 (1992); XP002946373.

Patro, B., et al; "Acid-Induced Ring Opening of α-[Bis(methylthio)methylene]alkyl Cyclopropyl Ketones: A Novel Route to Substituted Cyclopentanones through Carbocationic cyclizations"; *J. Org. Chem.,* vol. 57, No. 8, pp. 2257-2263 (1992); XP002476379.

Merz, A., et al; "Phase-transfer-catalyzed Production of Sulfur Ylides in an Aqueous System"; *Angew. Chem. Internat. Edit.,* vol. 12, No. 10; pp. 845-846 (1973); XP002476380.

Galardon, E., et al; "Asymmetric Cyclopropanation of Alkenes and Diazocarbonyl Insertion Into S-H Bonds Catalyzed by a Chiral Porphyrin Ru(II) Complex"; *Tetrahedron Letters,* vol. 39, No. 16; pp. 2333-2334 (1998); XP004111165.

Demonceau et al; "Cyclopropanation Catalyzed by $RuCl_2(PPh_3)_3$ and $OsCl_2(PPh_3)_3$"; *Tetrahedron Letters,* vol. 36, No. 46; pp. 8419-8422 (1995); XP005270638.

Demonceau, A., et al; "Cyclopropanation of Activated Olefins Catalysed by Ru-Phosphine Complexes"; *Tetrahedron Letters,* vol. 36, No. 20; pp. 3519-3522 (1995); XP004028095.

Kusuyama, Y.; "Solvolysis of 1-[*trans*-2-(*m*- or *p*-Substituted Phenyl)cyclopropyl]-1-methylethyl *p*-Nitrobenzoates[1]"; *Bulletin of the Chemical Society of Japan;* vol. 71, No. 3; pp. 685-691 (1998); XP009032176.

Kaiser, C., et al; "2-Substituted Cyclopropylamines. I. Derivatives and Analogs of 2-Phenylcyclopropylamine"; *Journal of Medicinal and Pharmaceutical Chemistry;* vol. 5; pp. 1243-1265 (1962); XP009032189.

Fuchs, R., et al; "Transmission of Electronic Effects by the Cyclopropane Ring. Ionization Constants of *m*- and *p*-Substituted β-Phenylpropionic, *cis*- and *trans*-2-Phenylcyclopropanecarboxylic Acids in 50% Ethanol"; Journal *of Organic Chemistry,* vol. 27, pp. 733-736 (1962); XP009032177.

Vallgarda, J., et al; "*trans*-2-Aryl-*N,N*-dipropylcyclopropylamines: Synthesis and Interactions with 5-$HT_{1A}$ Receptors"; *Journal of Medicinal Chemistry,* vol. 39, No. 7; pp. 1485-1493 (1996); XP002262871.

Database Beilstein; Beilstein Institute for Organic Chemistry, Frankfurt-Main, DE; Database Accession No. BRN 2583176 (Abstr); & Fuchs; Bloomfield: *J. Org. Chem.;* vol. 28; pp. 910-911 (1963); XP002476383.

Database Beilstein; *Beilstein Institute for Organic Chemistry,* Frankfurt-Main, DE; Database Accession No. BRN 2598637 (Abstr); & White, W.L., et al; *J. Chem. Soc. C*; pp. 2062-2068 (1971); XP002476384.

Filler, R., et al; "New Reactions of Polyfluoroaromatic Compounds. Part II. Polyfluoroaralkyl Amines[1]"; *Journal of the Chemical Society, Section C: Organic Chemistry;* pp. 2062-2068 (1971); XP009102773.

Coutts, R.T., et al; "Neurochemical and Neuropharmacological Properties of 4-Fluorotranylcypromine"; *Cellular and Molecular Neurobiology,* vol. 7, No. 3; pp. 271-290 (1987); XP009103506.

Houben-Weyl; *Methoden der Organischen Chemie,* fourth edition, vol. VIII, pp. 467-469 (1952); XP002489140.

Matsuda, F., et al; "Total Synthesis of (+)-Pederine. A Simple Synthetic Method for N-(1-Methoxyalkyl) Amides"; *Tetrahedron Letters,* vol. 23, No. 39; pp. 4043-4046 (1982); XP002489133.

Debruin, K.E., et al; "A New Route to N-Monosubstituted Thioamides Utilizing Phosphoramidothionates as Reagents for the Thioamidation of Carboxylic Acids"; *J. Org. Chem.;* vol. 55, No. 25; pp. 6091-6098 (1990); XP002489134.

Alabaster, R.J., et al "Synthesis of 6-(3-Aryl-2-propenyl)-2,3-dihydro-5-hydroxybenzofuran Derivatives by Cross Coupling Reactions"; *Synthesis;* pp. 598-603 (1989); XP002489135.

Wenkert, E., et al; "131. Synthesis of 2-Cycloalkenones (Parts of 1,4-Diacyl-1,3-butadiene Systems) and of a heterocyclic Analogue by Metal-Catalyzed Decomposition of 2-Diazoacylfurans"; *Helvetica Chimica ACTA,* vol. 70; pp. 1429-1438 (1987); XP002489136.

Newcomb, M., et al; "Picosecond Radical Kinetics. Ring Openings of Phenyl Substituted Cyclopropylcarbinyl Radicals"; *J. Am. Chem. Soc.;* vol. 114, No. 27; pp. 10915-10921 (1992); XP002489137.

Burger, A., et al; "Arylcycloalkylamines. I. 2-Phenylcyclopropylamine"; *J. Am. Chem. Soc.;* vol. 70, pp. 2198-2201 (1948); XP002489138.

Silverman, R.B., et al; "Evidence for a Hydrogen Atom Transfer Mechanisms or a Proton/Fast Electron Transfer Mechanism for Monoamine Oxidase"; *J. Org. Chem.;* vol. 57; pp. 6373-6374 (1992); XP002489139.

Database Beilstein; Beilstein Institute for Organic Chemistry, Frankfurt-Main, DE; Database Accession No. BRN 8407766 (Abstract) & M. Newcomb et al; *Canadian Journal of Chemistry;* vol. 77, No. 5/6; pp. 1123-1136 (1999); XP002489141.

PROCESS FOR THE PREPARATION OF CYCLOPROPYL CARBOXYLIC ACID ESTERS AND DERIVATIVES

This application is a continuation of application Ser. No. 10/275,547, filed Nov. 7, 2002, U.S. Pat. No. 7,122,695, the entire content of which is hereby incorporated by reference in this application.

FIELD OF THE INVENTION

The present invention relates to a novel process for the preparation of certain cyclopropyl carboxylic acid esters and other cyclopropyl carboxylic acid derivatives; a novel process for the preparation of dimethylsulfoxonium methylide and dimethylsulfonium methylide; to the use of certain cyclopropyl carboxylic acid esters in a process for the preparation of intermediates that can be used in the synthesis of pharmaceutically active entities; and to certain intermediates provided by these processes.

DESCRIPTION OF THE INVENTION

In a first aspect the invention therefore provides a process for the preparation of a compound of formula (I):

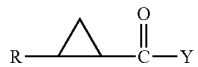
(I)

wherein:
R is phenyl substituted with one or more halogen;
Y is $OR^1$, where $R^1$ is a straight chain alkyl, branched allyl, cycloalkyl, or a substituted bicycloheptyl group (eg bornyl), which comprises contacting a compound of formula (II):

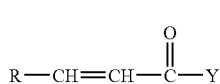
(II)

where R and Y are as defined above, with dimethylsulfoxonium methylide in the presence of a solvent.

Suitably the solvent is a polar solvent, preferably dimethyl sulfoxide. Suitably, the reaction is carried out at −10° C.-90° C., preferably 25° C.

The dimethylsulfoxonium methylide can be prepared by reacting a trimethylsulfoxonium salt with a solid strong base, preferably in solid form, in dimethyl sulfoxide at ambient or an elevated temperature. Suitably, the base is a metal hydroxide, eg NaOH, LiOH, or alkali metal hydride, eg NaH. Preferably the base is sodium hydroxide.

Preferably, trimethylsulfoxonium iodide is stirred with sodium hydroxide powder in dimethyl sulfoxide (in the absence of a phase transfer catalyst), optionally under nitrogen, at 20-25° C. for 90 minutes. Alternatively, the dimethylsulfoxonium methylide can be prepared from a trimethylsulfoxonium salt (preferably iodide or chloride) using sodium hydroxide in dimethyl sulfoxide with a phase transfer catalyst, for example tetrabutyl-n-ammonium bromide, or with other strong bases, such as alkali metal hydrides, in dimethyl sulfoxide.

A compound of formula (II) can be prepared by reacting a compound of formula (III):

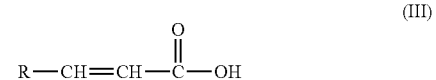
(III)

where R is as defined above, with a suitable chlorinating agent in the presence of an inert solvent and an optional catalyst at at a temperature of 0-200° C. Preferably Y is $OR^1$, the chlorinating agent is thionyl chloride, the inert solvent is toluene, and the catalyst is pyridine. Suitably the reaction temperature is 70° C. The resulting acid chloride is then reacted with YH or $Y^-$, (where $Y^-$ is an anionic species of Y), Y is as defined above, optionally at an elevated temperature, such as 100° C.

A compound of formula (III) can be prepared using standard chemistry, for example by contacting a compound of formula (IV):

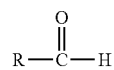
(IV)

where R is as defined above, with malonic acid in the presence of pyridine and piperidine at an elevated temperature, preferably 50-90° C.

A compound of formula (I) can be hydrolysed using basic hydrolysis to yield a compound of formula (V):

(V)

where R is as defined above. For example, ester groups are preferably removed by basic hydrolysis using an alkali metal hydroxide, such as sodium hydroxide or lithium hydroxide, or quaternary ammonium hydroxide in a solvent, such as water, an aqueous alcohol or aqueous tetrahydrofuran, at a temperature from 10-100° C. Most preferably the base is sodium hydroxide, the solvent is ethanol, and the reaction temperature is 50° C.

A compound of formula (V) can be used to generate a compound of formula (VI):

(VI)

where R is as defined above, by reaction with thionyl chloride or another suitable chlorinating agent in the presence of toluene, or another suitable solvent, and an optional catalyst, preferably pyridine, at 0-200° C. Preferably the temperature is to 65-70° C.

A compound of formula (VI) can be used in the synthesis of a compound of formula (VII):

(VII)

where R is as defined above, by reaction with an alkali metal azide (preferably sodium azide) in the presence of a phase transfer catalyst (preferably tetra-n-butylammonium bromide), aqueous potassium carbonate and an inert solvent (preferably toluene). Preferably the reaction temperature is 0-10° C.

A compound of formula (VII) can be used in the synthesis of a compound of formula (VIII):

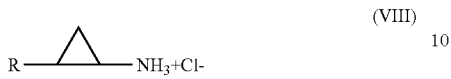
(VIII)

where R is as defined above, by rearrangement in toluene at temperatures between 0° C. and 200° C., preferably at a reaction temperature of 90-100° C., after which the isocyanate intermediate is reacted with hydrochloric acid at elevated temperatures, preferably 85-90° C.

An unprotonated parent amine (free base) of formula (IX):

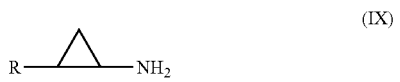
(IX)

where R is as defined above, can be liberated by adjusting the pH of an aqueous solution of the salt of a compound of formula (VIII) to 10 or more. This can then be converted to other salts of organic acids or inorganic acids, preferably mandelic acid. The R-(−)-mandelic acid salt of a compound of formula (IX) can be generated by addition of R-(−)-mandelic acid at ambient or an elevated temperature to a solution of a compound of formula (IX) in a solvent, preferably ethyl acetate. Preferably the temperature is 20° C.

Suitably R is phenyl optionally substituted by one or more halogen atoms. Preferably, R is phenyl substituted by one or more fluorine atoms. More preferably R is 4-fluorophenyl or 3,4-difluorophenyl.

Preferably Y is D-menthoxy, or more preferably, L-menthoxy.

Compounds of formulae (I) to (IX) can exist in different isomeric forms (such as cis/trans, enantiomers, or diastereoisomers). The process of this invention includes all such isomeric forms and mixtures thereof in all proportions.

Where Y is chiral, a compound of formula (I) will be a mixture of diastereoisomers and can be resolved to yield a diastereomerically-enriched compound of formula (Ia):

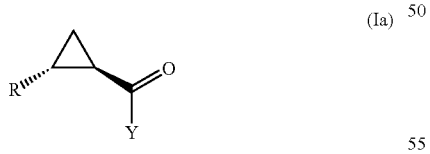
(Ia)

where R and Y are as defined above, by crystallisation or by chromatographic methods. Preferably the crystallisation is carried out in situ following the synthesis of a compound of formula (I), as described above, by heating the crude reaction mixture until total or near-total dissolution is achieved, then cooling at an appropriate rate until sufficient crystals of the desired quality are formed. The crystals are then collected by filtration. Alternatively, the resolution can be carried out in any other suitable solvent, such as a hydrocarbon, eg heptane by extracting a compound of formula (I) into a suitable amount of the solvent, heating the extracts until total dissolution is achieved, then cooling at an appropriate rate until sufficient crystals of the desired quality are formed. Optionally the organic extracts can be washed with water, dried over magnesium sulfate and filtered prior to the crystallisation described above.

A compound of formula (Ia) can be hydrolysed to yield a compound of formula (Va):

(Va)

where R is as defined above, using the method described above for the hydrolysis of a compound of formula (I) to yield a compound of formula (V).

A compound of formula (Va) can be used to generate a compound of formula (VIa):

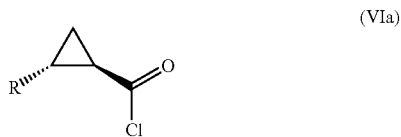
(VIa)

where R is as defined above, using the method described above for the conversion of a compound of formula (V) to yield a compound of formula (VI).

A compound of formula (VIa) can be used in the synthesis of a compound of formula (VIIa):

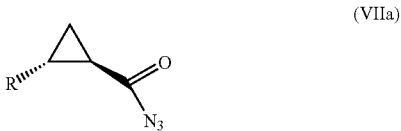
(VIIa)

where R is as defined above, using the method described above for the conversion of a compound of formula (VI) to yield a compound of formula (VII).

A compound of formula (VIIa) can be used in the synthesis of a compound of formula (VIIIa):

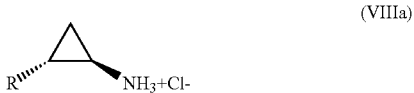
(VIIIa)

where R is as defined above, using the method described above for the conversion of a compound of formula (VII) to yield a compound of formula (VIII).

A compound of formula (VIIIa) can be used in the synthesis of a compound of formula (IXa):

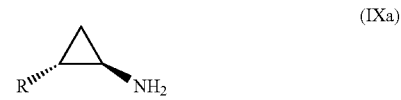
(IXa)

where R is as defined above, using the method described above for the conversion of a compound of formula (VIII) to yield a compound of formula (IX).

The R-(−)-mandelic acid salt of a compound of formula (IXa) can be generated using the method described above for the generation of the mandelic acid salt of a compound of formula (IX).

Novel compounds form a further aspect of the invention. In a further aspect the invention therefore provides compounds of formula (I), (Ia), (II), (III), (V), (Va), (VI), (VIa), (VII), (VIIa), (VIII), (VIIIa), (IX) and (IXa) as defined above.

Particularly preferred compounds include:
- (1R,2S,5R)-2-isopropyl-5-methylcyclohexyl trans-2-(3,4-difluorophenyl)cyclopropanecarboxylate;
- (1R,2S,5R)-2-isopropyl-5-methylcyclohexyl trans-(1R,2R)-2-(3,4-difluorophenyl)cyclopropane carboxylate;
- (1R,2S,5R)-2-isopropyl-5-methylcyclohexyl (E)-3-(3,4-difluorophenyl)-2-propenoate;
- (E)-3-(3,4-difluorophenyl)-2-propenoic acid;
- (E)-3-(3,4-difluorophenyl)-2-propenoyl chloride;
- trans-(1R,2R)-2-(3,4-difluorophenyl)cyclopropanecarboxylic acid;
- trans-(1R,2R)-2-(3,4-difluorophenyl)cyclopropanecarbonyl chloride;
- trans-(1R,2R)-2-(3,4-difluorophenyl)cyclopropanecarbonyl azide;
- trans-(1R,2S)-2-(3,4-difluorophenyl) cyclopropyl amine; and
- trans-(1R,2S)-2-(3,4-difluorophenyl)cyclopropanaminium (2R)-2-hydroxy-2-phenylethanoate

EXAMPLES

The invention is illustrated by the following non-limiting examples.

Example 1

This example illustrates the preparation of (E)-3-(3,4-difluorophenyl)-2-propenoic acid A stirred mixture of pyridine (15.5 kg) and piperidine (0.72 kg) were heated to 90° C. Malonic acid (17.6 kg) was added, followed by slow addition, over 50 minutes, of 3,4-difluorobenzaldehyde (12.0 kg). The reaction mixture was stirred at 90° C. for a further 4 hours and 36 minutes. Water (58.5 kg) was added and 32 litres of the pyridine/water mixture then was distilled out of the reactor under reduced pressure. The reaction mixture was acidified to pH 1 with 37% hydrochloric acid (6.4 kg) over a 40-minute period, then cooled to 25° C. with strong stirring. The solids were collected by filtration, washed twice with 1% hydrochloric acid (34.8 L per wash), once with water (61 L) and then deliquored thoroughly in the filter. The product was then dried under vacuum at 40° C. for 24 hours and 40 minutes, affording 13.7 kg of the crystalline product.

Example 2

This example illustrates the preparation of (E)-3-(3,4-difluorophenyl)-2-propenoyl chloride.

A stirred mixture of (E)-3-(3,4-difluorophenyl)-2-propenoic acid (8.2 kg), toluene (7.4 kg) and pyridine (0.18 kg) was heated to 65° C. and then thionyl chloride (7.4 kg) was added over 30 minutes. The reaction was stirred for a further 2 h 15 minutes after the addition was complete, then diluted with toluene (8.7 kg). Excess thionyl chloride, sulfur dioxide and hydrogen chloride were then distilled out, together with toluene (10 L), under reduced pressure, yielding a solution of the (E)-3-(3,4-difluorophenyl)-2-propenoyl chloride (approximately 9 kg) in toluene.

Example 3

This example illustrates the preparation of (1R,2S,5R)-2-isopropyl-5-methylcyclohexyl (E)-3-(3,4-difluorophenyl)-2-propenoate.

A solution of L-menthol (7.1 kg) in toluene (8.5 kg) was added over a 20 minute period to the solution of (E)-3-(3,4-difluorophenyl)-2-propenoyl chloride (prepared as in Example 2) and pyridine (0.18 kg, 2.28 mol) stirring at 65° C. The reaction mixture was stirred at 65° C. for a further 4 hours and 40 minutes after the addition was complete, then cooled to 25° C. and stirred for a 14 hours. The solution was diluted with toluene (16 kg), washed with 5% aqueous sodium chloride (6.4 kg), then 6% sodium hydrogen carbonate (6.47 kg), then water (6.1 kg). The solution was dried azeotropically by distillation of the solvent (20 L) under reduced pressure. Dimethyl sulfoxide (33.9 kg) was added and the remaining toluene was distilled off under reduced pressure, affording 47.3 kg of a solution of (1R,2S,5R)-2-isopropyl-5-methylcyclohexyl (E)-3-(3,4-difluorophenyl)-2-propenoate (approx. 13.3 kg) in dimethyl sulfoxide.

Example 4

This example illustrates a method of preparing dimethylsulfoxonium methylide (dimethyl(methylene)oxo-$\lambda^6$-sulfane).

Sodium hydroxide powder (1.2 kg), prepared by milling sodium hydroxide pellets in a rotary mill through a 1 mm metal sieve, and trimethylsulfoxonium iodide (6.2 kg) were stirred in dimethyl sulfoxide (25.2 kg) under a nitrogen atmosphere at 25° C. for 90 min. The solution was used directly in the preparation of (1R,2S,5R)-2-isopropyl-5-methylcyclohexyl trans-2-(3,4-difluorophenyl)cyclopropanecarboxylate.

Example 5

This example illustrates a method of preparing dimethylsulfonium methylide (dimethyl(methylene)-$\lambda^4$-sulfane).

Sodium hydroxide powder (970 mg), prepared by milling sodium hydroxide pellets in a rotary mill through a 1 mm metal sieve, and trimethylsulfonium iodide (4.66 g) were stirred in dimethyl sulfoxide (17 ml) under a nitrogen atmosphere at 20-25° C. for 10 min. The solution was used directly in the preparation of (1R,2S,5R)-2-isopropyl-5-methylcyclohexyl trans-2-(3,4-difluorophenyl)cyclopropanecarboxylate.

Example 6

This example illustrates the preparation of (1R,2S,5R)-2-isopropyl-5-methylcyclohexyl trans-2-(3,4-difluorophenyl)cyclopropanecarboxylate A solution of (1R,2S,5R)-2-isopropyl-5-methylcyclohexyl 3,4-difluorophenyl)-2-propenoate (approximately 8.6 kg) in dimethyl sulfoxide (approximately 27.9 kg) was added with stirring over 20 minutes to a mixture of dimethylsulfoxonium methylide (approximately 2.6 kg, prepared as described above), sodium iodide ((E)-3-(approximately 4.2 kg), water (approximately 500 g) and sodium hydroxide (approximately 56 g) in dimethylsulfoxide (27.7 kg) at 25° C. The reaction mixture was stirred for a further 2 hours and 50 minutes at 25° C., then used directly for the preparation of (1R,2S,5R)-2- isopropyl-5-methylcyclohexyl trans-(1R,2R)-2-(3,4-difluorophenyl)cyclopropanecarboxylate.

Example 7

This example illustrates the preparation of (1R,2S,5R)-2-isopropyl-5-methylcyclohexyl trans-(1R,2R)-2-(3,4-difluorophenyl)cyclopropanecarboxylate A crude solution of (1R,2S,5R)-2-isopropyl-5-methylcyclohexyl trans-2-(3,4-difluorophenyl)cyclopropanecarboxylate produced as described in example 6 was heated with stirring from 25° C. to 50° C. over a 1 hour period and the temperature was maintained for a further hour. The mixture was then cooled with stirring from 50° C. to 35° C. over 4 hours, kept at 35° C. for 1 hour, then cooled to 26° C. over 4 hours, kept at 26° C. for 1 hour, then cooled to 19° C. over 3 hours and kept at 19° C. for 5 hours and 10 minutes. The product crystallised and was collected by filtration, affording a crystalline solid (2.7 kg) which was shown to contain a mixture of (1R,2S,5R)-2-isopropyl-5-methylcyclohexyl trans-(1R,2R)-2-(3,4-difluorophenyl)cyclopropanecarboxylate (1.99 kg) and (1R,2S,5R)-2-isopropyl-5-methylcyclohexyl trans-(1S,2S)-2-(3,4-difluorophenyl)cyclopropanecarboxylate (85 g).

Example 8

This example illustrates an alternative method of preparing (1R,2S,5R)-2-isopropyl-5-methylcyclohexyl trans-(1R,2R)-2-(3,4-difluorophenyl)cyclopropanecarboxylate n-Heptane (82.5 L) was distilled under reduced pressure from a solution of (1R,2S,5R)-2-isopropyl-5-methylcyclohexyl trans-2-(3,4-difluorophenyl)cyclopropanecarboxylate (14.3 kg, 44.4 mol) in heptane (128.6 L). The mixture was then cooled from 34° C. to 24° C. over a period of 3 hours and 20 minutes. Seed crystals of (1R,2S,5R)-2-isopropyl-5-methylcyclohexyl trans-(1R,2R)-2-(3,4-difluorophenyl)cyclopropanecarboxylate were then added and the mixture was cooled to 0° C. over a period of 5 hours and 50 minutes. Filtration afforded the product as a crystalline solvent wet solid (7.05 kg) which was shown to contain a mixture of (1R,2S,5R)-2-isopropyl-5-methylcyclohexyl trans-(1R,2R)-2-(3,4-difluorophenyl)cyclopropanecarboxylate (4.7 kg) and (1R,2S,5R)-2-isopropyl-5-methylcyclohexyl trans-(1S,2S)-2-(3,4-difluorophenyl)cyclopropanecarboxylate (1.1 kg).

Example 9

This example illustrates a method of preparing trans-(1R,2R)-2-(3,4-difluorophenyl)cyclopropanecarboxylic acid.

(1R,2S,5R)-2-isoPropyl-5-methylcyclohexyl trans-(1R,2R)-2-(3,4-difluorophenyl)cyclopropanecarboxylate (9.6 kg, 91.8% diastereomeric excess) was dissolved in ethanol (13.8 kg) and heated with stirring to 46° C. 45% Aqueous sodium hydroxide (3.1 kg) was added over a 20 minute period and the mixture was stirred for a further 2 hours and 27 minutes. Solvent (28 L) was distilled out of the mixture under reduced pressure, then the mixture was cooled to 24° C. and diluted with water (29.3 kg), after which the liberated menthol was extracted into toluene (3 washes of 3.3 kg each). The remaining aqueous material was acidified to pH 2 with 37% hydrochloric acid (3.3 L) and the product was extracted into toluene (8.6 kg, then 2 more washes of 4.2 kg and 4.3 kg). The combined toluene extracts were washed with 1% hydrochloric acid (4.9 L), then diluted with further toluene (4.2 kg) and azeotropically dried by distillation of the solvent (25 L) under reduced pressure. A final dilution with toluene (24.2 kg) was followed by distillation of the solvent under reduced pressure (10 L) affording a solution containing trans-(1R,2R)-2-(3,4-difluorophenyl)cyclopropanecarboxylic acid (approximately 3.45 kg) suitable for the production of trans-(1R,2R)-2-(3,4-difluorophenyl)cyclopropanecarbonyl chloride.

Example 10

This example illustrates a method of preparing trans-(1R,2R)-2-(3,4-difluorophenyl)cyclopropanecarbonyl chloride.

Pyridine (70 ml) was added to a solution of trans-(1R,2R)-2-(3,4-difluorophenyl)cyclopropanecarboxylic acid (approximately 3.45 kg) in toluene (approximately 12-15 kg) prepared as described above, and the mixture was then heated to 65° C. Thionyl chloride (2.3 kg) was added over a period of 1 hour and the mixture was stirred at 70° C. for 3 hours. Thionyl chloride (0.5 kg) was added and the mixture was stirred a further 2 hours at 70° C. A final aliquot of thionyl chloride (0.5 kg) was added and the reaction mixture was stirred for 1 hour at 70° C., then cooled to 40° C. Periodic additions of toluene (45 kg, 3 additions of 15 kg each) were made during distillation of solvent (approximately 60 L) from the mixture under reduced pressure, then the solution of trans-(1R,2R)-2-(3,4-difluorophenyl)cyclopropanecarbonyl chloride (approximately 3.8 kg) in toluene (approximately 6-9 L) was cooled to 20° C.

Example 11

This example illustrates a method of preparing trans-(1R,2R)-2-(3,4-difluorophenyl)cyclopropanecarbonyl azide.

A solution of trans-(1R,2R)-2-(3,4-difluorophenyl)cyclopropanecarbonyl chloride (approximately 3.8 kg) in toluene (approximately 6-9 L) at 1° C. was added over a period of 74 minutes to a mixture of sodium azide (1.24 kg), tetrabutylammonium bromide (56 g) and sodium carbonate (922 g) in water (6.2 kg), stirring at 1.5° C. The mixture was stirred at 0° C. for 1 hour and 55 minutes, then the aqueous layer was diluted with cold water (3.8 kg), stirred briefly, then separated. The toluene layer was washed once more at 0° C. with water (3.8 kg), then with 20% aqueous sodium chloride (3.8 L), then stored at 3° C. for further use.

Example 12

This example illustrates a method of preparing trans-(1R,2S)-2-(3,4-difluorophenyl)cyclopropylamine.

A cold solution of trans-(1R,2R)-2-(3,4-difluorophenyl)cyclopropanecarbonyl azide prepared as described in Example 11 was added over a period of 41 minutes to toluene (6.0 kg) stirring at 100° C. The mixture was stirred for a further 55 minutes at 100° C., then cooled to 20° C. and added over a period of 2 hours and 15 minutes to hydrochloric acid (3M, 18.2 kg) stirring at 80° C. After 65 minutes the solution was diluted with water (34 kg) and cooled to 25° C. The toluene layer was removed and the aqueous layer was basified to pH 12 with 45% sodium hydroxide (3.8 kg) and the product was then extracted into ethyl acetate (31 kg) and washed twice with water (13.7 kg per wash), affording a solution containing trans-(1R,2S)-2-(3,4-difluorophenyl)cyclopropylamine (2.6 kg, 91.8% enantiomeric excess) in ethyl acetate (29.5 L).

Example 13

This example illustrates a method of preparing trans-(1R,2S)-2-(3,4-difluorophenyl)cyclopropanaminium (2R)-2-hydroxy-2-phenylethanoate.

R-(−)-Mandelic acid (2.26 kg) was added to a solution containing trans-(1R,2S)-2-(3,4-difluorophenyl)cyclopropylamine (2.6 kg, 91.8% enantiomeric excess), stirring at 17° C. in ethyl acetate (45.3 L). The mixture was stirred at 25° C. for 3 hours and 8 minutes, then filtered and washed twice with ethyl acetate (13.8 kg total). The crystalline product was dried at 40° C. under reduced pressure for 23 hours, affording trans-(1R,2S)-2-(3,4-difluorophenyl)cyclopropanaminium (2R)-2-hydroxy-2-phenylethanoate (4.45 kg).

The invention claimed is:
1. The intermediate compounds;
   trans-(1R,2R)-2-(3,4-difluorophenyl)cyclopropanecarbonyl azide; and
   trans-(1R,2S)-2-(3,4-difluorophenyl)cyclopropanaminium (2R)-2-hydroxy-2-phenylethanoate.

* * * * *